US011191842B2

(12) United States Patent
Yang et al.

(10) Patent No.: US 11,191,842 B2
(45) Date of Patent: *Dec. 7, 2021

(54) INJECTABLE THERMORESPONSIVE POLYELECTROLYTES

(71) Applicant: Northwestern University, Evanston, IL (US)

(72) Inventors: Jian Yang, Evanston, IL (US); Robert Van Lith, Chicago, IL (US); Guillermo Ameer, Chicago, IL (US)

(73) Assignee: Northwestern University, Evanston, IL (US)

( * ) Notice: Subject to any disclaimer, the term of this patent is extended or adjusted under 35 U.S.C. 154(b) by 291 days.

This patent is subject to a terminal disclaimer.

(21) Appl. No.: 15/819,921

(22) Filed: Nov. 21, 2017

(65) Prior Publication Data

US 2018/0154009 A1 Jun. 7, 2018

Related U.S. Application Data

(62) Division of application No. 13/982,980, filed as application No. PCT/US2012/023293 on Jan. 31, 2012, now Pat. No. 9,844,600.

(Continued)

(51) Int. Cl.
*A61K 47/60* (2017.01)
*C08G 63/676* (2006.01)
(Continued)

(52) U.S. Cl.
CPC ............ *A61K 47/60* (2017.08); *A61K 9/0024* (2013.01); *A61K 47/34* (2013.01); *A61P 43/00* (2018.01);
(Continued)

(58) Field of Classification Search
CPC ..... C08L 67/07; C08G 63/676; C08F 290/06; C08F 290/061; C08F 290/08; C08F 290/14; C08F 290/141; C08F 283/01
See application file for complete search history.

(56) References Cited

U.S. PATENT DOCUMENTS 5,124,421 A 6/1992 Ulbrich et al.
5,702,717 A 12/1997 Cha et al.
(Continued)

FOREIGN PATENT DOCUMENTS

WO WO 2007075502 7/2007
WO WO 2010127254 11/2010
WO WO 2012106317 8/2012

OTHER PUBLICATIONS van Lith (Diazeniumdiolated Protamine Sulfate as Biomodal Nitric Oxide Delivery System for Vascular Repair. Transactions of the Annual Meeting of the Society for Biomaterials, vol. 32, Issue: Annual Meeting of the Society for Biomaterials: Giving Life to a World of Materials, 2010, vol. 1, p. 163).*

(Continued)

*Primary Examiner* — Brieann R Johnston
(74) *Attorney, Agent, or Firm* — Casimir Jones, S.C.; David W. Staple

(57) ABSTRACT

Provided herein are compositions, devices, and systems comprising copolymers of an N-alkyl acrylamide residue and a polyester comprising citric acid, polyethylene glycol, and glycerol 1,3-diglycerolate diacrylate, and methods of use and manufacture thereof.

13 Claims, 11 Drawing Sheets

Related U.S. Application Data

(60) Provisional application No. 61/438,071, filed on Jan. 31, 2011.

(51) Int. Cl.
  *A61K 9/00* (2006.01)
  *A61K 47/34* (2017.01)
  *C12N 5/00* (2006.01)
  *C08L 67/07* (2006.01)
  *C08F 283/01* (2006.01)
  *A61P 43/00* (2006.01)

(52) U.S. Cl.
  CPC .......... *C08F 283/01* (2013.01); *C08G 63/676* (2013.01); *C08L 67/07* (2013.01); *C12N 5/0068* (2013.01); *C12N 2539/10* (2013.01)

(56) References Cited

U.S. PATENT DOCUMENTS

| | | | |
|---|---|---|---|
| 5,807,581 | A | 9/1998 | Rosenblatt et al. |
| 6,030,634 | A | 2/2000 | Wu et al. |
| 6,458,889 | B1 | 10/2002 | Trollsas et al. |
| 6,486,213 | B1* | 11/2002 | Chen .................. A61K 9/0014 514/772.1 |
| 6,833,408 | B2 | 12/2004 | Sehl et al. |
| 6,841,617 | B2 | 1/2005 | Jeong et al. |
| 7,919,112 | B2* | 4/2011 | Pathak .................. A61K 35/12 424/423 |
| 9,200,109 | B2* | 12/2015 | Cohn .................. A61L 24/0042 |
| 9,844,600 | B2 | 12/2017 | Yang et al. |
| 2005/0281883 | A1 | 12/2005 | Daniloff et al. |
| 2006/0122322 | A1 | 6/2006 | Chrisstoffels et al. |
| 2006/0204555 | A1* | 9/2006 | Yang .................. A61K 31/74 424/443 |
| 2008/0096975 | A1 | 4/2008 | Guan et al. |
| 2008/0264867 | A1 | 10/2008 | Mika et al. |
| 2009/0325859 | A1* | 12/2009 | Ameer .................. A61L 27/18 514/1.1 |

OTHER PUBLICATIONS

Gyawali (Citric acid-derived in situ crosslinkable biodegradable polymers for cell delivery, Biomaterials, 2010, 31(34), pp. 9092-9105).*

Choi (Thermosensitive poly(N-isopropylacrylamide)-b-poly(ε-caprolactone) nanoparticles for efficient drug delivery system. Polymer, 2006, 47, pp. 4571-4580).*

Dai (The pH-induced thermosensitive poly(NIPAAm-co-AAc-co-HEMA)-g-PCL micelles used as a drug carrier, J Mater Sci: Mater Med, 2010, 21, 1881-1890).*

Ando et al., "Protamines. Isolation, characterization, structure and function," Molecular Biology, Biochemistry & Biophysics 1973; 12: 1-114.

Bar et al., "Shrinkage behaviour of hydrophobic hydrogel during dehydration," J Food Eng 2002; 55(3): 193-199.

Bulmus et al., "Stimuli-responsive properties of conjugates of N-isopropylacrylamide-co-acrylic acid oligomers with alanine, glycine and serine mono-, di- and tri-peptides," J Control Release 2001; 76: 265-274.

Chen et al., "Polymer-protein conjugates. II. Affinity precipitation separation of human immunogammaglobulin by a poly(N-isopropylacrylamide)-protein A conjugate," Biomaterials 1990; 11(9): 631-634.

Deible et al., "Creating molecular barriers to acute platelet deposition on damaged arteries with reactive polyethylene glycol," J Biomed Mater Res 1998; 41(2): 251-256.

Delgado et al., "The uses and properties of PEG-linked proteins," Crit Rev Therapeut Drug Carrier Syst 1992; 9: 249-304.

Dincer et al., "Radical copolymerization of N-isopropylacrylamide with anhydrides of maleic and citraconic acids," Eur Polym J 2002; 38: 2143-2152.

Evora et al., "Protamine induces endothelium-dependent vasodilatation of the pulmonary artery," The Annals of Thoracic Surgery 1995; 60(2): 405-410.

Fujimoto et al., "Synthesis, characterization and therapeutic efficacy of a biodegradable, thermoresponsive hydrogel designed for application in chronic infarcted myocardium," Biomaterials 2009; 30(26): 4357-4368.

Garthwaite, "Glutamate, nitric oxide and cell-cell signalling in the nervous system," Trends in Neurosciences 1991; 14(2): 60-67.

Guan et al., "Protein-reactive, thermoresponsive copolymers with high flexibility and biodegradability," Biomacromolecules 2008; 9(4): 1283-1292.

Han et al., "Surface characteristics and biocompatibility of lactide-based poly(ethylene glycol) scaffolds for tissue engineering," J Biomater Sci Polym Ed 1998; 9(7): 667-680.

Hibbs et al., "Synthesis of nitric oxide from L-arginine: a recently discovered pathway induced by cytokines with antitumour and antimicrobial activity," Research in Immunology 1991; 142(7): 565-569.

Ignarro, "Heme-dependent activation of soluble guanylate cyclase by nitric oxide: regulation of enzyme activity by porphyrins and metalloporphyrins," Seminars in Hematology 1989; 26(1): 63-76.

Katre el al., "The conjugation of proteins with polyethylene glycol and other polymers: Altering properties of proteins to enhance their therapeutic potential," Adv Drug Delivery Rev 1993; 10: 91-114.

Kaul et al., "Polymeric-based perivascular delivery of a nitric oxide donor inhibits intimal thickening after balloon denudation arterial injury: role of nuclear factor-kappaB1," Journal of the American College of Cardiology 2000; 35(2): 493-501.

Kesim et al., "Functional bioengineering copolymers. II. Synthesis and characterization of amphiphilic poly(N-isopropyl acrylamide-co-maleic anhydride) and its macrobranched derivatives," Polymer 2003; 44: 2897-2909.

Kharitonov et al., "Kinetics of Nitrosation of Thiols by Nitric Oxide in the Presence of Oxygen," Journal of Biological Chemistry 1995; 270(47): 28158-28164.

Kim et al., "Swelling induced detachment of chondrocytes using RGD-modified poly(N-isopropylacrylamide) hydrogel beads," Biotechnol Prog 2002; 18(3): 495-500.

Kim et al., "Synthesis and characterization of injectable poly(N-isopropylacrylamide-co-acrylic acid) hydrogels with proteolytically degradable cross-links.," Biomacromolecules, 2003, 4(5): 1214-1223.

Kim et al., "Graft copolymerization of glycerol 1,3-diglycerolate diacrylate onto poly(3-hydroxyoctanoate) to improve physical properties and biocompatibility," Int J Biol Macromol. Oct. 1, 2008;43(3):307-13.

Lee et al., "Improved Planar Amperometric Nitric Oxide Sensor Based on Platinized Platinum Anode. 2. Direct Real-Time Measurement of NO Generated from Porcine Kidney Slices in the Presence of l-Arginine, l-Arginine Polymers, and Protamine," Analytical Chemistry 2004; 76(3): 545-551.

Lee et al., "In situ-gelling, erodible N-isopropylacrylamide copolymers," Macromol. Biosci. 2005, 5(7): 629-635.

Li et al., "Heparin and protamine stimulate the production of nitric oxide," The Journal of Cardiovascular Surgery 1996; 37(5): 445-452.

Li et al., "Recruitment of multiple cell lines by collagen-synthetic copolymer matrices in corneal regeneration," Biomaterials, 2005, 26(16): 3093-3104.

Loh et al., Novel poly(N-isopropylacrylaminde)-poly[®-3-hydroxybutyrate]-poly(N-isopropylacrylaminde) triblock copolymer surface as a culture substrate for human mesenchymal stem cells. Soft Matter. Jun. 2009; 5(15):2937-2946.

Matsuda, "Molecular design of functional artificial extracellular matrix: thermoresponsive gelatin," Jpn J Artif Organs 1999; 28: 242-245.

Mitchell-Koch et al., "Light-activated transfer of nitric oxide from a porous material," Angewandte Chemie-International Edition 2004; 43(21): 2806-2809.

(56) References Cited

OTHER PUBLICATIONS

Monji et al., "A novel immunoassay system and bioseparation process based on thermal phase separating polymers," Appl Biochem Biotechnol 1987; 14(2): 107-120.
Naeini et al., "Poly(citric acid)-block-poly(ethylene glycol) copolymers—new biocompatible hybrid materials for nanomedicine," Nanomedicine: Nanotechnology, Biology, and Medicine, 2010;6(4):556-562.
Ohya et al., "Artificial extracellular matrix design in tissue engineering: Synthesis of thermoresponsive hyaluronic acid and its supramolecular organization," Jpn J Artif Organs 2000; 29: 446-451.
Ohya et al., "Material design for an artificial extracellular matrix: Cell entrapment in poly (N-isopropylacrylamide) (PNIPAM)-grafted gelatin hydrogel," J Artif Organs 2001; 4: 308-314.
Palmer et al., "Vascular endothelial cells synthesize nitric oxide from L-arginine," Nature 1988; 333: 664-666.
Park et al., "Bacterial adhesion on PEG modified polyurethane surfaces," Biomaterials 1998; 19: 851-859.
Pevni et al., "Protamine induces vasorelaxation of human internal thoracic artery by endothelial NO-synthase pathway," The Annals of Thoracic Surgery 2000; 70(6): 2050-2053.
Qiu et al., "Study of the Core-Shell Nanoparticle Formed through the "Coil-to-Globule" Transition of Poly(N-isopropylacrylamide) Grafted with Poly(ethylene oxide)," Macromolecules 1997; 30(25): 7921-7926.
Saavedra et al., "Localizing Antithrombotic and Vasodilatory Activity with a Novel, Ultrafast Nitric Oxide Donor," Journal of Medicinal Chemistry 1996; 39(22): 4361-4365.
Singh et al., "Mechanism of Nitric Oxide Release from S-Nitrosothiols," Journal of Biological Chemistry 1996; 271(31): 18596-18603.
Sogo et al., "Inhibition of Human Platelet Aggregation by Nitric Oxide Donor Drugs: Relative Contribution of cGMP-Independent Mechanisms," Biochemical and Biophysical Research Communications 2000; 279(2): 412-419.
Stile et al., "Thermo-responsive peptide-modified hydrogels for tissue regeneration," Biomacromolecules, 2001, 2(1): 185-194.
Strauss et al., "Effects of alkyl group size and counterion type on the behavior of copolymers of maleic anhydride and alkyl vinyl ethers. 2. Fluorescence of dansylated copolymers," J Phys Chem 1978; 82(14): 1627-32.
Suggs et al., "Platelet adhesion on a bioresorbable poly(propylene fumarate-co-ethylene glycol) copolymer," Biomaterials 1999; 20(7): 683-690.
Takakura et al., "Protamine sulfate causes endothelium-independent vasorelaxation via inducible nitric oxide syn-thase pathway," Journal Canadian d'Anesthesie 2006; 53(2): 162-167.
Virtanen et al., "Grafting of Poly(N-isopropylacrylamide) with Poly(ethylene oxide) under Various Reaction Conditions," Macromolecules 2000; 33(2): 336-341.
Wang et al., "Novel thermosensitive hydrogel injection inhibits post-infarct ventricle remodelling," Eur J Heart Fail 2009; 11: 14-19.
Xiao et al., "High-Capacity Hydrogen and Nitric Oxide Adsorption and Storage in a Metal-Organic Framework," Journal of the American Chemical Society 2007; 129(5): 1203-1209.
Yang et al., "Novel Citric Acid-Based Biodegradable Elastomers for Tissue Engineering," Adv Mater 2004; 16(6): 511-516.
Yang et al., "Synthesis and evaluation of poly(diol citrate) biodegradable elastomers," Biomaterials 2006; 27(9): 1889-1898.
Zakir et al., "Functional copolymers of N-isopropylacrylamide for bioengineering applications," Prog Polym Sci 2007; 32(5): 534-59.
Zhang et al., "Thermoresponsive Micellization of Poly(ethylene glycol)-b-poly(N-isopropylacrylamide) in Water," Macromolecules 2005; 38(13): 5743-5747.
Zhao et al., "Modulating the Mechanical Properties of Poly(diol citrates) via the Incorporation of a Second Type of Crosslink Network," Jouranl Applied Polymer Science, 2009, 114:1464-1470.
Zhu et al., "Aggregation of Block Copolymer Microgels of Poly(N-isopropylacrylamide) and Poly(ethylene glycol)," Macromolecules 1999; 32(6): 2068-2070.
Zhu et al., "Effect of Heating Rate on Nanoparticle Formation of Poly(N-isopropylacrylamide)-Poly(ethylene glycol) Block Copolymer Microgels," Langmuir 2000; 16(22): 8543-8545.
International Search Report and Written Opinion for PCT/US2012/023293, dated May 21, 2012, 12 pages.
Supplementary European Search Report for EP12741537, dated Sep. 28, 2016, 5 pages.

* cited by examiner

INJECTABLE THERMORESPONSIVE POLYELECTROLYTES

CROSS REFERENCE TO RELATED APPLICATIONS

This application is a divisional of Ser. No. 13/982,980, filed Oct. 14, 2013, now allowed, which is a national phase application under 35 U.S.C. § 371 of PCT International Application No. PCT/US2012/023293, filed Jan. 31, 2012, which claims the benefit of and priority to U.S. Provisional Application No. 61/438,071, filed on Jan. 31, 2011, each of which is hereby incorporated by reference in its entirety.

FIELD

Provided herein are compositions, devices, and systems comprising thermoresponsive, biodegradable elastomeric materials, and methods of use and manufacture thereof.

BACKGROUND

Two- and three-dimensional polymer/hydrogel matrices provide a diverse scaffold that can be modified and refined for various purposes. Hydrogels can be applied to various medical, engineering, biological and chemical applications, such as drug or chemical delivery, tissue engineering, cell transplantation, wound healing and rheology modification (See, e.g.: Wu et al. (U.S. Pat. No. 6,030,634); Trollsas et al. (U.S. Pat. No. 6,458,889); Sehl et al. (U.S. Pat. No. 6,833,408); Stile & Healy (Biomacromolecules, 2001, 2(1): 185-194); Kim & Healy (Biomacromolecules, 2003, 4(5): 1214-1223); Li et al. (Biomaterials, 2005, 26: 3093-3104); Rosenblatt et al. (U.S. Pat. No. 5,807,581); Ulbrich et al. (U.S. Pat. No. 5,124,421); Lee & Vernon (Macromol. Biosci. 2005, 5(7):629-635); Cha et al. (U.S. Pat. No. 5,702,717); Jeong et al. (U.S. Pat. No. 6,841,617); each of which is herein incorporated by reference in its entirety).

Various kinds of thermoresponsive N-isopropylacrylamide (NIPA) copolymers are among an important class of bioengineering materials that have been the subject of many extensive investigations in the field of modern macromolecular bioengineering and biotechnology (See, e.g.: Monji N, Hoffman A S. Appl Biochem Biotechnol 1987; 14:107-20; Chen J-P, Hoffman A S. Biomaterials 1990; 11:631-4; Kim M R, Jeong J H, Park T G. Biotechnol Prog 2002; 18:495-500; Strauss U P, Schlesinger M S. J Phys Chem 1978; 82:1627-32; Katre N V. Adv Drug Delivery Rev 1993; 10:91-114; Delgado C, Francis G E, Fisher D. Crit Rev Therapeut Drug Carrier Syst 1992; 9:249-304; Kesim H, Rzaev ZMO, Dincer S, Piskin E. Polymer 2003; 44:2897-909; Dincer S., Koseli, V., Kesim H., Rzaev ZMO, Piskin E. Eur Polym J 2002; 38:43-52; Bulmus V. Patir S, Tuncel A, Piskin E. J Control Release 2001; 76:265-74; Lee B H, Vernon B. Macromol Biosci 2005; 5:629-635; Guan J, Hong Y, Ma Z, Wagner W R. Biomacromolecules 2008; 9:1283-1292.; Wang T, Wu D, Jiang X, Li X, Zhang J, Zheng Z, Zhuo R, Jiang H, Huang C. Eur J Heart Fail 2009; 11:14-19; Fujimoto K L, Ma Z, Nelson D M, Hashizume R, Guan J, Tobita K, Wagner W R. Biomaterials 2009; 30:4357-4368; Yang J, Webb J A, Ameer G A. Adv Mater 2004; 16:511-516; Yang J, Webb A, Pickerill S. Hageman G, Ameer G A. Biomaterials 2006; 27:1889-1898; herein incorporated by reference in their entireties).

PEG is commonly incorporated into medical implants to resist protein adsorption, platelet adhesion, and bacterial adhesion (Deible C R, Beckman E J, Russell A J, Wagner W R. J Biomed Mater Res 1998; 41:251-256; Han D K, Park ICD, Hubbell J A, Kim Y H. J Biomater Sci Polym Ed 1998; 9:667-680; Park K D, Kim Y S, Han D K, Kim Y H, Lee E H, Suh H, Choi K S. Biomaterials 1998; 19:851-859; Suggs L T, West J L, Mikos A G. Biomaterials 1999; 20:683-690; herein incorporated by reference in their entireties). Various copolymerization methods (Zakir M. O. Rzaev, Sevil Dincer, Erhan P. Prog Polym Sci 2007; 32:534-59) have been developed to synthesize the double hydrophilic copolymers such as PEG-b-PNIPA (Zhu P W, Napper D R Macromolecules 1999; 32:2068-2070; Zhu P W, Napper D H. Langmuir 2000; 16:8543-8545; Zhang W Q, Shi L Q, Wu K, An Y L. Macromolecules 2005; 38:5743-5747; herein incorporated by reference in their entireties) or PEG-g-PNIPA (Qiu X, Wu C. Macromolecules 1997; 30:7921-7926; Virtanen J, Baron C, Tenhu H. Macromolecules 2000; 33:336-341; herein incorporated by reference in their entireties) by modifying PEG end-groups such as PEG-Br or amino-terminated PEG as macroinitiator or PEO methacrylate as macromonomer. The solubilizing effect of PEG on the shrinking backbone can compete with hydrophobic interactions in poly(NIPA) due to dehydration at a temperature above 35° C. (Bar A, Ramon O, Cohen Y, Mizrahi S. J Food Eng 2002; 55:193-199).

Thermoresponsive materials such as PNIPAM-derivatized gelatin (PNIPAM-gelatin) (Matsuda T. Jpn J Artif Organs 1999; 28:242-245) and PNIPA-derivatized hyaluronic acid (PNIPAM-HA) (Ohya S, Nakayama Y, Matsuda T. Jpn J Artif Organs 2000; 29:446-451; herein incorporated by reference in its entirety) have been functioned as cell-adhesive and cell non-adhesive matrix to encapsulate bovine smooth muscle cells for cell therapies; however, the entrapped cells died in hydrogel (Ohya, Nakayama, Matsuda. J Artif Organs 2001; 4:308-314; herein incorporated by reference in its entirety).

SUMMARY

Provided herein are thermoresponsive and biodegradable elastomeric materials, including copolymers and compositions and structures, such as hydrogels, comprising the copolymers. The copolymers remain fluid at and below room temperature, solidify at physiological temperature, and bind to biological molecules. The copolymers also degrade and dissolve at physiological conditions in a time-dependent manner, which may be important for removal of the hydrogel, for example, after an applied surgical or medical procedure. In some embodiments, copolymers described herein and their degradation products are biocompatible, for example and without limitation, they are not cytotoxic.

According to one embodiment, copolymers comprise an N-isopropylacrylamide residue (an N-isopropylacrylamide monomer incorporated into a polymer), a citric acid residue, a polyethylene glycol, and a multifunctional linker. The copolymer comprises a polyester linkage in its backbone. According to one non-limiting embodiment, the copolymer is prepared from at least five components: N-isopropylacrylamide or an N-alkyl acrylamide in which the alkyl is methyl, ethyl, propyl, isopropyl or cyclopropyl, citric acid, a polyethylene glycol, and a multifunctional linker. In some embodiments, a copolymer comprises 2 or more (e.g., 2, 3, 4, 5) of: N-isopropylacrylamide or an N-alkyl acrylamide in which the alkyl is methyl, ethyl, propyl, isopropyl or cyclopropyl, citric acid, a polyethylene glycol, and a multifunctional linker. Copolymers of the present invention are not limited by these components, and may comprise different and/or additional components within the scope of the invention. In certain embodiments, the copolymer is prepared by polymerizing the N-alkyl acrylamide with a polyester macromer. In specific embodiments, the polyester macromer is a polycitrate-co-polyethylene glycol macromer, comprising glycerol 1,3-diglycerolate diacrylate residues and varying numbers of citric acid and polyethylene glycol units/residues. Typically, each component contributes to the desired physical properties of the hydrogel to enable an injectable material for delivering drugs or chemicals, encapsulating and transplanting cells, and injecting into empty cavities for wounds or tissue repair. In some embodiments, the citric acid component of the copolymer binds to positively charged compounds including biomolecules such as protamine sulfate and/or other bioactive or biocompatible materials or factors. In certain embodiments, the composition of each component in the hydrogel determines the lower critical solution temperature (LCST) of the hydrogel. At a temperature less than the LCST, the hydrogel flows easily and can be injected into the desired shape. When the temperature is increased above the LCST, the hydrogel solidifies and retains the shape. Once solidified, the hydrogel is highly flexible and relatively strong at physiological temperature.

According to one embodiment, the polyester component within the macromer introduces the degradability and hydrophilicity of the copolymer. For complete removal of the copolymer, the copolymer includes hydrolytically-cleavable bonds that results in soluble, non-toxic by-products, even above the LCST of the non-degraded copolymer. In one embodiment, the copolymer has a lower critical solution temperature below 37° C. and, in particular embodiments, between 30° C. and 35° C.

Positively charged biomolecules or other compounds, such as proteins, carbohydrates, glycoproteins, etc. can be incorporated into the copolymer through ionic interactions with the negatively charged carboxylate groups. In certain embodiments, protamine sulfate is a suitable compound, for instance and without limitation, about 10 mg/ml protamine sulfate. In certain embodiments the protamine sulfate is N-diazeniumdiolated.

A composition comprising the copolymer described herein and an aqueous solvent, for example and without limitation, water, saline and phosphate-buffered saline also is provided. In some embodiments, compositions also include an active agent, such as, without limitation, one or more of an antiseptic, an antibiotic, an analgesic, an anesthetic, a chemotherapeutic agent, a clotting agent, an anti-inflammatory agent, a metabolite, a cytokine, a chemoattractant, a hormone, a steroid, a protein and a nucleic acid. In one embodiment, where the composition comprises a clotting agent, one example of a clotting agent is desmopressin. A biological material, such as a cell or a virus particle may also be incorporated into the composition.

A method is provided of making a thermosensitive copolymer, for example, a co-polymer described herein, the method comprising co-polymerizing N-isopropylacrylamide with a citric acid-co-polyethylene glycol prepolymer further comprising glycerol 1,3-diglycerolate diacrylate.

The citric acid-co-polyethylene glycol prepolymer can be prepared by any useful method, for example and without limitation by step growth polymerization. In order to prepare the copolymer of the present invention, it is useful to incorporate a multi-functional linker into the prepolymer. In some embodiments, glycerol 1,3-diglycerolate diacrylate is used. Different feed ratios of citric acid, polyethylene glycol, and glycerol 1,3-diglycerolate diacrylate can be used. In one embodiment a molar ratio of 1:1.8:0.2 is used.

The N-isopropylacrylamide and poly (citric acid-co-polyethylene glycol) prepolymer can be co-polymerized by any useful polymerization method, for example and without limitation by free-radical polymerization. Various feed ratios of the poly (citric acid-co-polyethylene glycol) prepolymer and N-isopropylacrylamide can be used. For example but without limitation, the ratio of poly (citric acid-co-polyethylene glycol) prepolymer and N-isopropylacrylamide (wt:wt) can be 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, or 95:5. In certain embodiments, the ratio is 25:75, 50:50, or 75:25. In the particular embodiments, the feed ratio is 50:50.

According to another embodiment a method of growing cells is provided, comprising introducing cells into a copolymer composition described herein to produce a cell construct and incubating the cell construct under conditions suitable for growth of the cells. The composition can comprise cell growth media to facilitate cell growth within the composition. The cell construct can be administered to a patient (placed in a patient's body at a desired location), such as a human patient. In another embodiment, the composition is administered to a patient without cells, but so that the patient's cells migrate into the composition. The composition can be administered by a subcutaneous injection into the desired site within the patient. To facilitate this, the composition may comprise one or more of a cytokine, a cell growth or differentiation agent and a metabolite. The composition also may include an active agent, such as, without limitation, an antiseptic, an analgesic, an anesthetic and an antibiotic. As above, the copolymer can be complexed with protamine sulfate and/or N-diazeniumdiolated protamine sulfate, for example and without limitation, at about 10 mg/ml.

In some embodiments, the present invention provides copolymers comprising: (a) an N-alkyl acrylamide residue; and (b) a polyester. In some embodiments, the polyester comprises one or more (e.g., each of): citric acid, polyethylene glycol, and glycerol 1,3-diglycerolate diacrylate. In some embodiments, the alkyl is selected from: methyl, ethyl, propyl, isopropyl and cyclopropyl. In some embodiments, the N-alkyl acrylamide residue comprises N-isopropylacrylamide. In some embodiments, the polyester consists of: citric acid, polyethylene glycol, and glycerol 1,3-diglycerolate diacrylate. In some embodiments, the copolymer has a lower critical solution temperature below 37° C. In some embodiments, the copolymer has a lower critical solution temperature of between 30° C. and 35° C. In some embodiments, the present invention provides a positively charged compound complexed to the copolymer. In some embodiments, the positively charged compound is protamine sulfate. In some embodiments, the positively charged compound is diazeniumdiolated. In some embodiments, the composition further comprises one or more active agents selected from: an antiseptic, an antibiotic, an analgesic, an anesthetic, a chemotherapeutic agent, a clotting agent, an anti-inflammatory agent, a metabolite, a cytokine, a chemoattractant, a hormone, a steroid, a protein, and a nucleic acid. In some embodiments, the composition further comprises one or more biological materials selected from a cell, a protein or a virus.

In some embodiments, methods are provided for manufacture of a thermosensitive copolymer comprising co-polymerizing an N-alkyl acrylamide in which the alkyl is one of methyl, ethyl, propyl, isopropyl and cyclopropyl; and a polyester comprising citric acid, polyethylene glycol, and glycerol 1,3-diglycerolate diacrylate. In some embodiments, the N-alkyl acrylamide is N-isopropylacrylamide. In some embodiments, the monomers are co-polymerized by free-radical polymerization.

In some embodiments, methods are provided for growing cells, comprising introducing cells into a copolymer of the present invention to produce a cell construct and incubating the culturing mixture under conditions suitable for growth of the cells. In some embodiments, cell growth media is provided. In some embodiments, methods further comprise administering the cell construct into a patient. In some embodiments, the patient is a human patient. In some embodiments, the composition is administered to a patient and patient's cells migrate into the composition. In some embodiments, the composition comprises one or more of a cytokine, a cell growth or differentiation agent and a metabolite. In some embodiments, the composition comprises one or more of an antiseptic, an analgesic, an anesthetic and an antibiotic.

DETAILED DESCRIPTION

Figure 1:
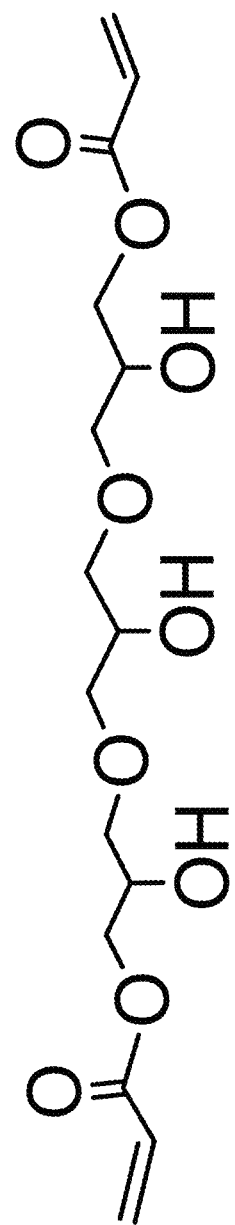
FIG. 1 shows the chemical structure of the multi-functional linker glycerol 1,3-diglycerol diacrylate.

According to embodiments of the compounds and compositions described herein, provided herein are injectable hydrogels that are biodegradable, elastomeric and thermoresponsive and which can easily take the shape of a cavity into which they are injected in advance of phase transition to solid. Biocompatible copolymers and compositions comprising such copolymers are provided. In certain embodiments, the copolymers and degradation products thereof are non-toxic and typically have an LCST between room temperature and 37° C. so that they are liquid at room temperature and gelled at 37° C. which facilitates their use in humans, for example for wound treatment and as a cellular growth matrix or niche. In some embodiments, the copolymers are injectable as a liquid at or below room temperature (about or exactly 25° C.) and are solid at body temperature (about or exactly 37° C.). These materials are useful for a number of purposes. For example, in treatment of patients, they may be used as an injectable stem cell niche for bone marrow transplants or for other transplantation settings; delivery vehicles for chemotherapy to tissue, such as, for example and without limitation, gut following tumor resections; sealants for pulmonary and neural applications as well as for emergency treatment of wounds. The materials also can find use as bulking agents for cosmetic applications or, even more generally, rheology modifiers. The copolymer comprises numerous ester linkages in its backbone so that the copolymers are erodible in situ. Certain degradation products of the polymer are soluble and non-toxic. In particular embodiments, the copolymer is amine-reactive so that it can conjugate with proteins, such as collagen. Active ingredients, such as drugs, can be incorporated into compositions comprising the copolymer.

In some embodiments, synthesized biodegradable thermoresponsive polyanions described herein are quickly solidified at 37° C. containing the media without shrinkage and conveniently implanted by injection in aqueous solution. The thermoresponsive polyelectrolyte with carboxylic groups complexes with cationic protein such as protamine sulfate or protein NO donor such as N-diazeniumdiolated protamine sulfate for controlled NO release.

According to certain embodiments, copolymers comprise four types of subunits/residues: 1) N-alkyl acrylamide in which the alkyl may comprise, but is not limited to: methyl, ethyl, propyl, isopropyl or cyclopropyl, for example N-isopropylacrylamide, as a thermosensitive component after polymerization; 2) citric acid 3) polyethylene glycol for improvement of hydrophilicity and 4) a multifunctional linker. In some embodiments, copolymers comprise 1, 2, or 3, of the above four types or subunits/residues alone or with additional types of subunits/residues.

The copolymers, compositions and components thereof are preferably biocompatible. By "biocompatible," it is meant that a polymer composition and its normal in vivo degradation products are cytocompatible and are substantially non-toxic and non-carcinogenic in a patient within useful, practical and/or acceptable tolerances. By "cytocompatible," it is meant that the copolymers or compositions are substantially non-toxic to cells and typically and most desirably can sustain a population of cells and/or the polymer compositions, devices, copolymers, and degradation products thereof are not cytotoxic and/or carcinogenic within useful, practical and/or acceptable tolerances. For example, a copolymer composition when placed in a human epithelial cell culture does not adversely affect the viability, growth, adhesion, and number of cells. In one non-limiting example, the co-polymers, compositions, and/or devices are "biocompatible" to the extent they are acceptable for use in a human or veterinary patient according to applicable regulatory standards in a given legal jurisdiction. In another example the biocompatible polymer, when implanted in a patient, does not cause a substantial adverse reaction or substantial harm to cells and tissues in the body, for instance, the polymer composition or device does not cause necrosis or an infection resulting in harm to tissues organs or the organism from the implanted compositions.

As used herein, a "polymer" is a compound formed by the covalent joining of smaller molecules, which are referred to herein as residues, or polymer subunits, when incorporated into a polymer. A "copolymer" is a polymer comprising two or more different residues. Prior to incorporation into a polymer, the residues typically are described as monomers. Non-limiting examples of monomers, in the context of the copolymer described herein, include: citric acid monomers, polyethylene glycol monomers, glycerol 1,3-diglycerolate diacrylate monomers, and N-alkyl acrylamide monomers. A monomer may be a macromer prepared from even smaller monomers, such as the polyethylene glycol macromer described herein. Polyester polymer backbones are polymer backbones containing two or more ester groups. A polyester linkage has an average of more than one ester units (—C(O)O—), as opposed to an ester linkage that has one ester unit. An example is a poly (citric acid—co-polyethylene glycol prepolymer as described herein.

Lower critical solution temperature (LCST) refers to the temperature below which the constituents of the hydrogel are soluble in water and above which the constituents are insoluble. When the LCST is reached, the polymer constituents in an aqueous solution will aggregate to form hydrogel. The LCST can be determined by measuring the change in transmittance with a UV-Vis spectrometer as a function of temperature (Advanced Drug Delivery Reviews (1998), 31: 197-221 and Annals N.Y. of Science, 1999, 875(1):24-35). LCST also can be determined by any other useful method—for example and without limitation by Differential Scanning Calorimetry. UV-Vis spectroscopy is used to measure LCTS in the examples below.

One aspect of the polymers described herein is that the LCST of these polymers is typically between 18° C. and about 37° C. so that the polymer can be distributed through the marketplace, stored and administered to a patient as a liquid at ambient temperatures (or, if necessary, maintained at a cool temperature with an ice-pack, refrigerator or other cooling device), and the polymer then gels as it warms past its LCST. Many polymers suitable for administration to patients require mixing of monomers immediately prior to use, which is undesirable for many reasons. For instance, it is impractical to ask doctors, nurses or technicians to mix monomers as they need the polymer. Further, monomers can have varying degrees of toxicity. The copolymers described herein do not require conducting a chemical reaction at the site of use and the copolymers can be washed free of monomer contamination prior to distribution in the marketplace. Lastly, the release of a portion of the aqueous phase during phase transition can facilitate local drug delivery in the excluded aqueous phase.

Another desirable physical quality of the polymers described herein is that, when ester linkages in the backbone are hydrolyzed (for instance over time in situ in a living system, such as a human patient), the released copolymer fragments are soluble (and as an additional benefit, non-toxic), facilitating safe degradation and clearance of the polymer over time in a living system such as a human body.

In one embodiment of the copolymer useful in humans or animals, the copolymer has a lower critical solution temperature below 37° C. For veterinary applications, the LCST can be slightly higher as the core body temperature of certain animals (e.g., cats, dogs, horses, cows, sheep and goats) is in the range of 38° C.-39° C.

In some medical or veterinary uses, the copolymers and compositions comprising the copolymers serve as adhesives or fillers. They may be applied to wounds or into body cavities or used as a tissue packing to apply compression. As such, embodiments of the copolymer solutions described herein are applied to wounds. In some embodiments, copolymers are applied with a warming compress, "heat pack," or other suitable means to ensure that the copolymer is maintained at a temperature above its LCST and thus remains gelled when in contact with any cooler areas of the body, typically the skin. As a hydrogel, embodiments of the copolymers disclosed herein may be contained in a composition comprising the copolymer and an aqueous solution that does not interfere substantially with the LCST and polymer structure in its intended use. For instance, in certain embodiments, the composition comprises any aqueous solvent, optionally pharmaceutically acceptable, including, without limitation, water, PBS, Saline, etc. As used herein, and "aqueous solvent", is an aqueous solution compatible with the copolymer which can be absorbed into the copolymer matrix. In some embodiments, the composition also comprises an active agent, biological or drug, such as, without limitation: antibiotics, clotting agents (without limitation, an antifibrinolytic, such as desmopressin/DDVAP), analgesics, anesthetics, antiseptics, anti-inflammatory agents, chemotherapeutic agents, metabolites, rheology modifiers, cytokines, chemoattractants, hormones, steroids, proteins (including enzymes), nucleic acids, cells, virus particles, nucleic acids, biomatrices or precursors thereof, or a foaming agent. In one embodiment, the composition comprises stem cells (such as adipose-derived stem cells) or other progenitor cells so that the composition is useful as a biodegradable tissue engineering scaffold. The composition, even without cells, is useful as a cell growth niche or scaffolding into which cells such as native stem/progenitor cells can migrate in situ. In such an embodiment, chemokines, cellular growth agents and cellular differentiation agents can be included within the composition to attract cells into the composition and promote cellular growth and differentiation when placed in situ.

According to particular embodiments, in its application to wound treatment, a clotting agent such as desmopressin is included in a polymer composition. An appropriate, e.g., pharmaceutically acceptable, foaming agent as are well-known in the relevant arts also may be included for the purpose of creating compression in a wound, whether exposed to a body surface in the case of (for example) puncture wounds or bullet wounds, or internal wounds, in which case, the polymer can be injected into or near a site of internal bleeding. As such, compositions find use in many situations, ranging from home use to stabilization of bleeding or massively bleeding patients in emergency and battlefield situations. In some embodiments, copolymers also find use during surgical procedures to apply compression and otherwise secure a site of injury, such as a portion of a patient's intestine, nasal passage or sinus cavity where a tumor or polyp has been removed or after other surgeries. The benefits of such a reversibly-gelling copolymer composition is that the composition can be removed simply by cooling, for example and without limitation, by flushing with cool (lower than the copolymer's LCST) flushing solution, such as water, saline or phosphate-buffered saline. Thus, while a wound and bleeding in a patient can be stabilized by application of the polymer, the polymer can be selectively eroded in an emergency room or during surgery simply by flushing with a cool (for example and without limitation, 0° C. to 30° C.) saline solution.

The properties of the hydrogels can be modulated, for example, by varying the feed ratios of the monomers during the synthesis of the CPEGD prepolymer, by varying the feed ratios of the CPEGD prepolymer and the NIPAM during the synthesis of the poly (citric acid-co-polyethylene glycol-N-isopropylacrylamide) copolymer, or by varying the concentration of the poly (citric acid-co-polyethylene glycol-N-isopropylacrylamide) copolymer prior to gel formation. In certain embodiments, the concentration of the copolymer is between 1 mg/ml and 250 mg/ml. In particular embodiments, the concentration of the copolymer is 40 mg/ml, 50 mg/ml, 60 mg/ml, 70 mg/ml, 80 mg/ml, 90 mg/ml, 100 mg/ml, 110 mg/ml, 120 mg/ml, 130 mg/ml, 140 mg/ml, 150 mg/ml, or 160 mg/ml. In some embodiments, the concentration of the copolymer is between 50 mg/ml and 100 mg/ml.

In a further embodiment, the composition serves as a cell growth medium. According to one embodiment, cells are introduced into a composition comprising a copolymer as described herein to produce a cell construct. The cell construct is incubated under conditions suitable for growth of the cells. That is, the cell construct can be placed in an incubator or into a patient so that the cells are maintained under adequate environmental conditions to permit the cells to survive, proliferate, differentiate and/or express certain products. "Cell growth" means that the cells survive and preferably, though not exclusively, divide and multiply. The composition may comprise cell growth media, which typically provides necessary nutrients and environmental conditions for cell growth. The cells may be introduced and incubated under conditions suitable for cell growth by introducing the composition into a patient and allowing native cells, such as stem cells to migrate into the composition. The composition can be administered by injecting the composition into the region requiring cellular growth or remodeling, such as a region of damaged tissue. In one non-limiting example, the damaged tissue is within the cardiac wall caused by a myocardial infarction and the composition is injected into the cardiac wall. In one variation of that embodiment, cytokines, chemoattractants, nutrients and/or cell differentiation factors are included in the composition. The composition may also contain one or more of an antiseptic, an analgesic, an anesthetic and an antibiotic (for example, for selection of the cells or to prevent bacterial growth in the composition).

In another aspect, this invention provides a facilitation of local delivery of nitric oxide (NO) and protamine (sulfate), for suppression of platelet aggregation/adhesion and proliferation of smooth muscle cells. NO has drawn a great deal of attention from the research community to understand its synthesis cascade and regulatory functions in vivo (Palmer, R. M. J.; Ashton, D. S.; Moncada, S., Nature 1988, 333, (6174), 664-666; Ignarro, L. J., Seminars in Hematology 1989, 26, (1), 63-76; Hibbs, J. B., Research in Immunology 1991, 142, (7), 565-569; Garthwaite, J., Trends in Neurosciences 1991, 14, (2), 60-67; herein incorporated by reference in their entireties). These findings aroused enormous efforts to develop NO-generating compounds such as N-diazeniumdiolates (Kaul, S.; Cercek, B.; Rengstrom, J.; Xu, X. P.; Molloy, M. D.; Dimayuga, P.; Parikh, A. K.; Fishbein, M. C.; Nilsson, J.; Rajavashisth, T. B., Journal of the American College of Cardiology 2000, 35, (2), 493-501; Saavedra, J. E.; Southan, G. J.; Davies, K. M.; Lundell, A.; Markou, C.; Hanson, S. R.; Adrie, C.; Hurford, W. E.; Zapol, W. M.; Keefer, L. K., Journal of Medicinal Chemistry 1996, 39, (22), 4361-4365; Sogo, N.; Magid, K. S.; Shaw, C. A.; Webb, D. J.; Megson, I. L., Biochemical and Biophysical Research Communications 2000, 279, (2), 412-419), nitrosothiols (Kharitonov, V. G.; Sundquist, A. R.; Sharma, V. S., Journal of Biological Chemistry 1995, 270, (47), 28158-28164; Singh, R. J.; Hogg, N.; Joseph, J.; Kalyanaraman, B., Journal of Biological Chemistry 1996, 271, (31), 18596-18603) and NO-metal complexes (Mitchell-Koch, J. T.; Reed, T. M.; Borovik, A. S., Angewandte Chemie-International Edition 2004, 43, (21), 2806-2809; Xiao, B.; Wheatley, P. S.; Zhao, X. B.; Fletcher, A. J.; Fox, S.; Rossi, A. G.; Megson, I. L.; Bordiga, S.; Regli, L.; Thomas, K. M.; Morris, R. E., Journal of the American Chemical Society 2007, 129, (5), 1203-1209; herein incorporated by reference in their entireties), with the aim of taking advantage of NO as a potential therapeutic agent. The use of materials described herein for local delivery of nitric oxide is highly desirable for prosthetic bypass grafts, catheters, stents, intracorporeal sensors and other blood contacting objects. It has been revealed that NO is extensively implicated in diverse in vivo functions in the human body, and considerable research has been devoted to synthesis and modification of artificial compounds to bear NO donor complexes such as N-diazeniumdiolate, nitrosohydroxyamine or nitrosothiol groups, which moieties can instantaneously produce NO under physiological conditions. Diazeniumdiolated protamine or protamine sulfate is thought to induce vasorelaxation and inhibition of smooth muscle cell proliferation by the dual effect of exogenous NO delivery and upregulation of endogenous NO production by vascular endothelial cells. The unique nature of protamine for endogenous NO induction makes this system still effective for local NO generation even after depletion of the exogenous NO moieties. The diazeniumdiolated protamine-encapsulating, NO-releasing system can easily provide for incorporation with any type of medical device via surface coating or embedding. Protamine, an L-arginine-rich protein (Ando, T.; Yamasaki, M.; Suzuki, K., Molecular Biology, Biochemistry & Biophysics 1973, 12, 1-114), has numerous guanidine groups that can potentially be converted into diazeniumdiolate moieties under highly pressurized NO atmosphere. Diazeniumdiolated compounds have been proven to dissociate and generate NO spontaneously upon proton contact, e.g. by placing the compound in physiological fluids. On the other hand, protamine, probably as an exogenous source of (poly)-L-arginine (Lee, Y.; Yang, J.; Rudich, S. M.; Schreiner, R. J.; Meyerhoff, M. E., Analytical Chemistry 2004, 76, (3), 545-551; herein incorporated by reference in its entirety), is expected to serve to stimulate local NO production by acting with endothelial cells (Pevni, D.; Gurevich, J.; Frolkis, I.; Keren, G.; Shapira, I.; Paz, J.; Kramer, A.; Locker, C.; Mohr, R., The Annals of Thoracic Surgery 2000, 70, (6), 2050-2053; Evora, P. R.; Pearson, P. J.; Schaff, H. V., The Annals of Thoracic Surgery 1995, 60, (2), 405-410; Li, J. M.; Hajarizadeh, H.; La Rosa, C. A.; Rohrer, M. J.; Vander Salm, T. J.; Cutler, B. S., The Journal of Cardiovascular Surgery 1996, 37, (5), 445-452; herein incorporated by reference in their entireties) and possibly smooth muscle cells (Takakura, K.; Mizogami, M.; Fukuda, S., Journal Canadien d'Anesthesie 2006, 53, (2), 162-167; herein incorporated by reference in its entirety), thus leading to anti-thrombosis and vasorelaxation.

Compositions comprising one or more copolymers described herein can be distributed for use in any suitable vessel. In one instance, the composition is packaged in a sealed container, from which the composition can be poured, squeezed or otherwise decanted, for example and without limitation, by use of a syringe. The vessel can be a bag, such as an IV bag. In another embodiment, the composition can be distributed in a syringe for immediate dispensation into a wound or body cavity/location. A syringe can be fitted with any type of needle, tip, tube, balloon device or other useful fitting for facilitating accurate placement of the solution in or around a desired delivery site, for example and without limitation, for delivery into the large intestine of a patient after removal of a tumor. In another embodiment, the composition and a pharmaceutically acceptable solvent is stored within a syringe at or below 4° C. and the syringe is fitted with a needle gauge sufficient to allow for injection without increased pressure but also prohibit back flow of the solution into the syringe after injection, such as, without limitation, a 16 through 23 G (gauge) needle, and in certain embodiments an 18 G or 20 G needle. Thus, methods of use embodying the above-described uses for a copolymer described herein and compositions comprising the copolymer are contemplated and embraced as part of the present invention.

In another use, a composition described herein can be used for cosmetic purposes, such as for a rheology modifier. Ingredients, including without limitation colorants, fragrances, flavors, and other ingredients listed herein, including active agents, may be included in the composition.

In some embodiments, kits and/or systems are provided comprising the copolymers and/or compositions provided herein with additional compositions, reagents, instructions, containers, cells, controls, buffers, etc.

EXPERIMENTAL

The following examples are provided for illustration purposes and are not intended to limit the scope of the present invention.

Example 1

Synthesis of Poly(Citric Acid-Co-Polyethylene Glycol) (CPEGD) Prepolymers

The general synthesis of citric acid-based prepolymers has been previously described (Yang J, Webb J A, Ameer G A. Adv Mater 2004; 16:511-516; Yang J, Webb A, Pickerill S. Hageman G, Ameer G A. Biomaterials 2006; 27:1889-1898; herein incorporated by reference in its entirety). For example, citric acid (Sigma-Aldrich, 99.5+%), PEG (400, Aldrich) and glycerol 1,3-diglycerolate diacrylate (Aldrich) with different feed molar ratios such as 1/1.8/0.2 were melted together at 130° C. while stirring for 30 minutes to perform the step growth polymerization. The structure of glycerol 1,3-diglycerolate diacrylate is shown in FIG. 1. The CPEGD prepolymers were obtained by lowering the reactive temperature to room temperature and directly used in the following reaction without further purification.

Example 2

Synthesis of Poly(Citric Acid-Co-PEG-N-Isopropylacrylamide) (CPN) Copolymers

Figure 2:
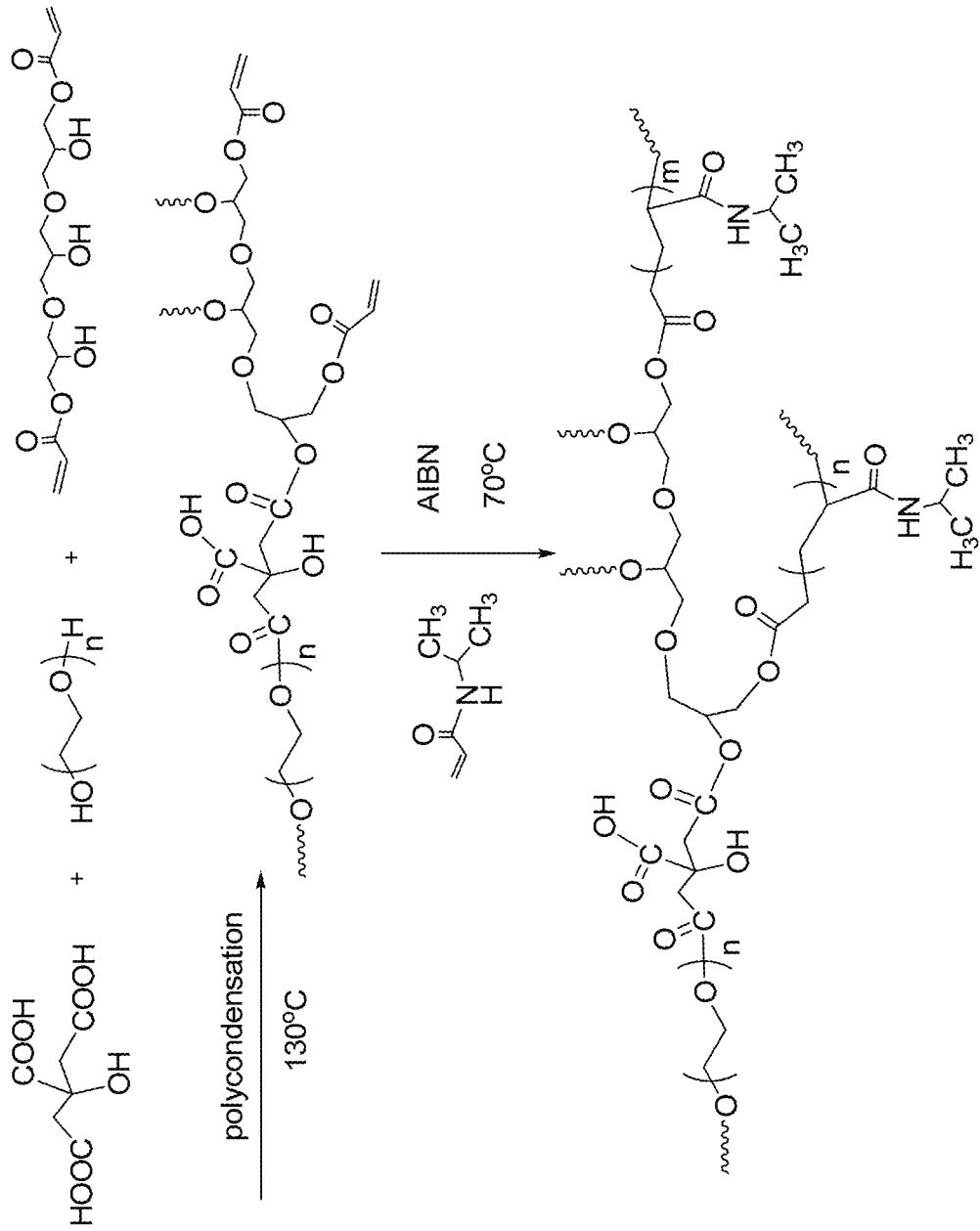
FIG. 2 is a schematic of the synthesis of poly (citric acid-co-PEG-co-NIPAM) copolymer.

The synthetic scheme for the synthesis of CPN copolymers is shown in FIG. 2. N-Isopropylacrylamide (NIPAM, Aldrich 98%) was purified by recrystallization from hexanes and dried under vacuum for 4 days, 2, 2'-Azobisisobutyronitrile (AIBN, Aldrich 98%) was purified by recrystallization from methanol. CPN copolymers with CPEGD/NIPAM feed ratios (w/w) of 25/75, 50/50 and 75/25 were synthesized by radical polymerization in 1,4-dioxane at 70° C. with AIBN radical initiator at constant total concentration of monomers under $N_2$. Briefly, the total monomer concentration was 2.78 mol/L in 1, 4-dioxane, and the AIBN concentration was ($6.5\times10-3$ mol/L). Appropriate quantities of monomers, 1,4-dioxane and AIBN were placed into a standard pyrex-glass tube, nitrogen was bubbled through the solution at room temperature for 15 min prior to the addition of the initiator to reduce oxygen content in the polymerization reaction. The copolymerization was conducted at 70° C. for 8 h under a nitrogen atmosphere. Subsequently, the copolymer was precipitated in an excess of diethyl ether, filtered, and then dried under reduced pressure. The yield was around 86%.

Figure 3:
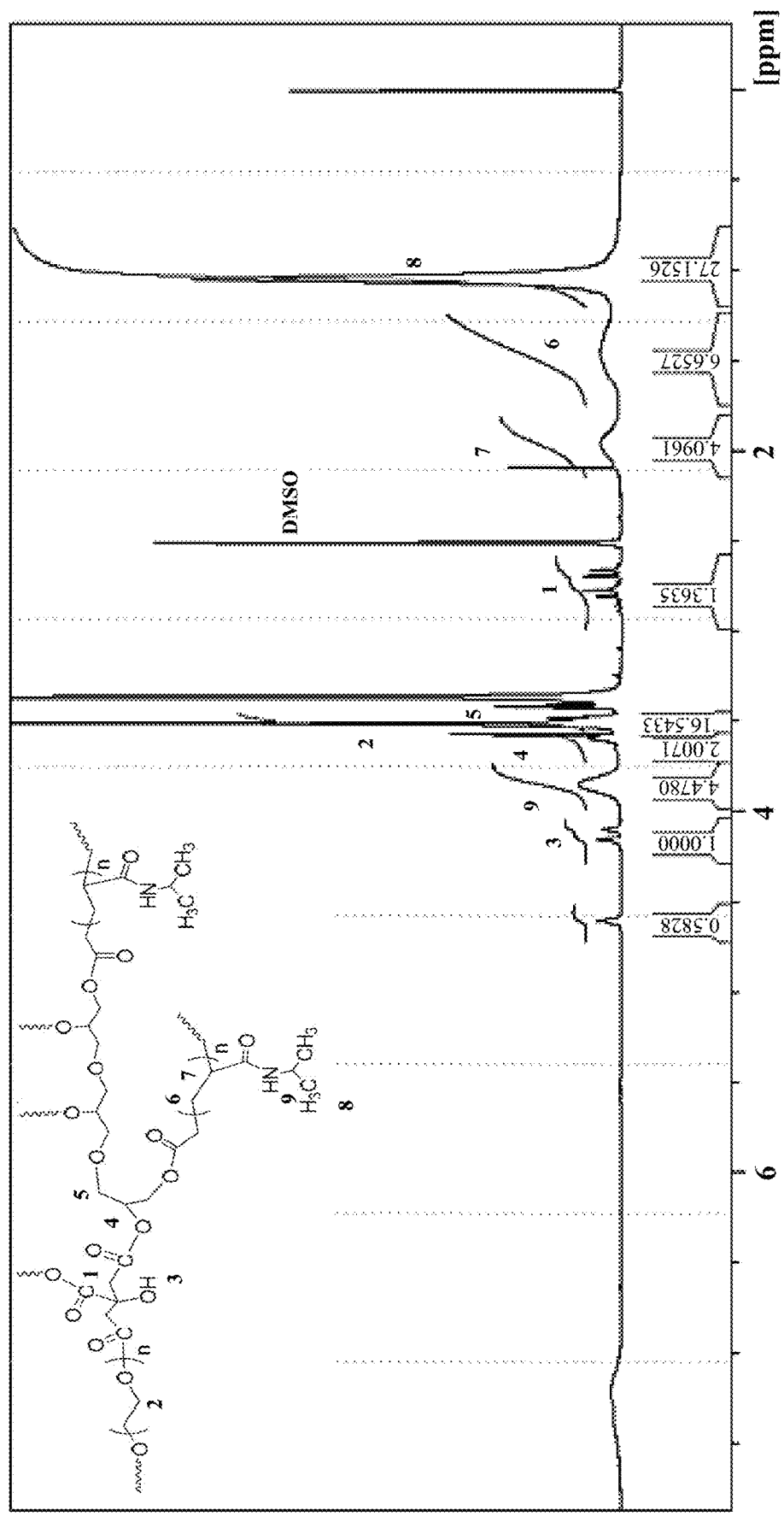
FIG. 3 shows the $^1$H NMR spectrum of the CPN55 copolymer is a schematic showing the diazeniumdiolation of protamine sulfate in room temperature (RT) under NO gas of 5 atm.

The synthesis of thermoresponsive CPN polyelectrolytes was confirmed by $^1$H NMR (FIG. 3), which contained proton peaks in agreement with the molecular structure of CPN copolymers.

Example 3

Phase Transition and pH Change of Thermoresponsive CPN Polyelectrolytes

The phase transition of thermoresponsive CPN polyelectrolyte solutions in water (10 wt %) were determined by measuring optical absorption at 550 nm over a temperature range of 25 to 45° C. at a heating rate of 1° C./min. The onset temperature of transition curve of each copolymer was seen as its lower critical solution temperature (LCST). The LCSTs of PNIPA homopolymer, CPEGD prepolymer, the mixture of PNIPA and CPEGD have also recorded as a comparison. The pH change of CPEGD prepolymers and CPN polyelectrolytes with different concentrations was measured using a pH-meter.

Figure 4:
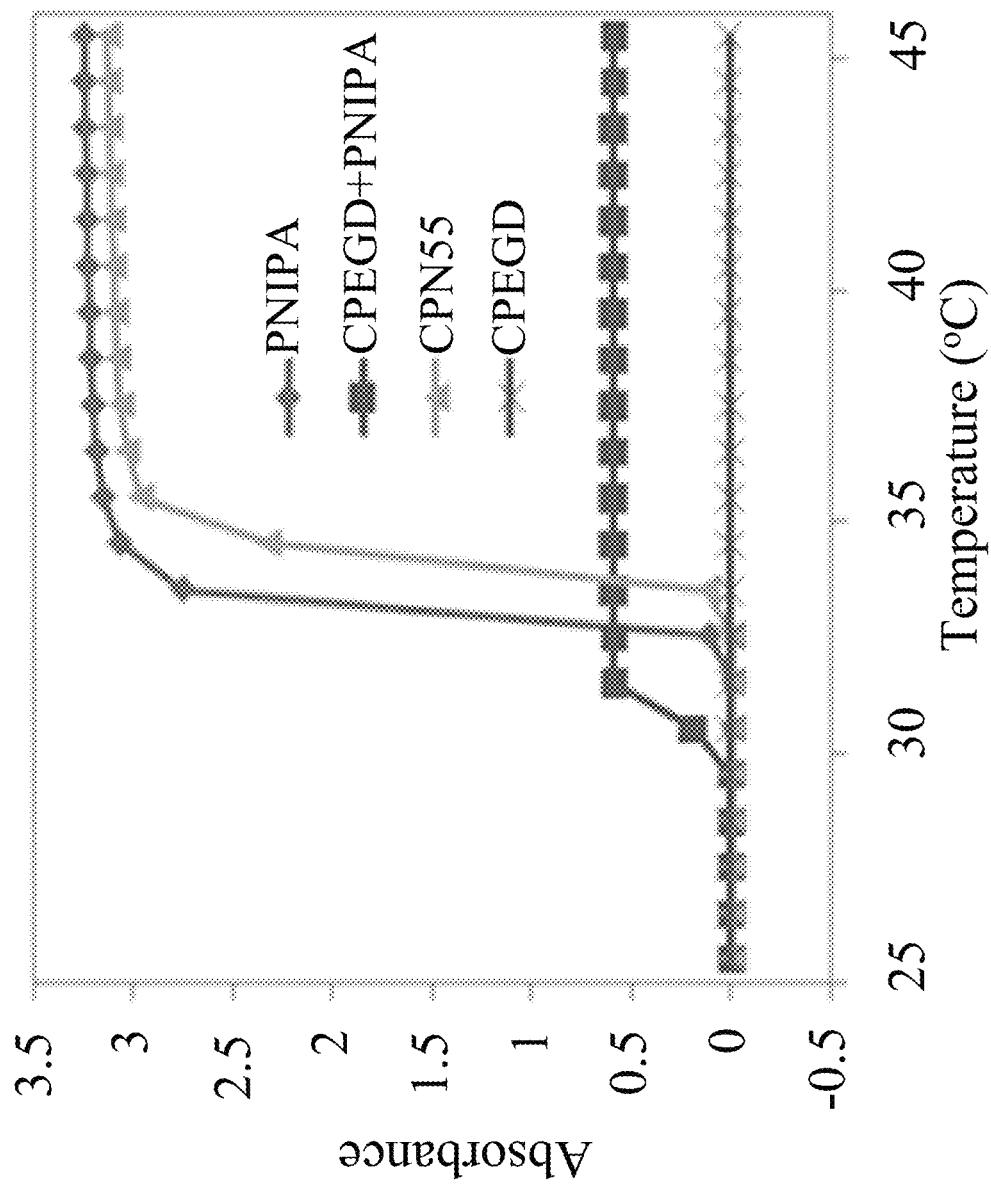
FIG. 4 shows phase transition curves of CPEGD prepolymer, PNIPAM homopolymer, CPN55 copolymer and the mixture of CPEGD and PNIPAM in aqueous solution as measured using a Jasco-815 CD spectrophotometer at 550 nm.
Figure 5:
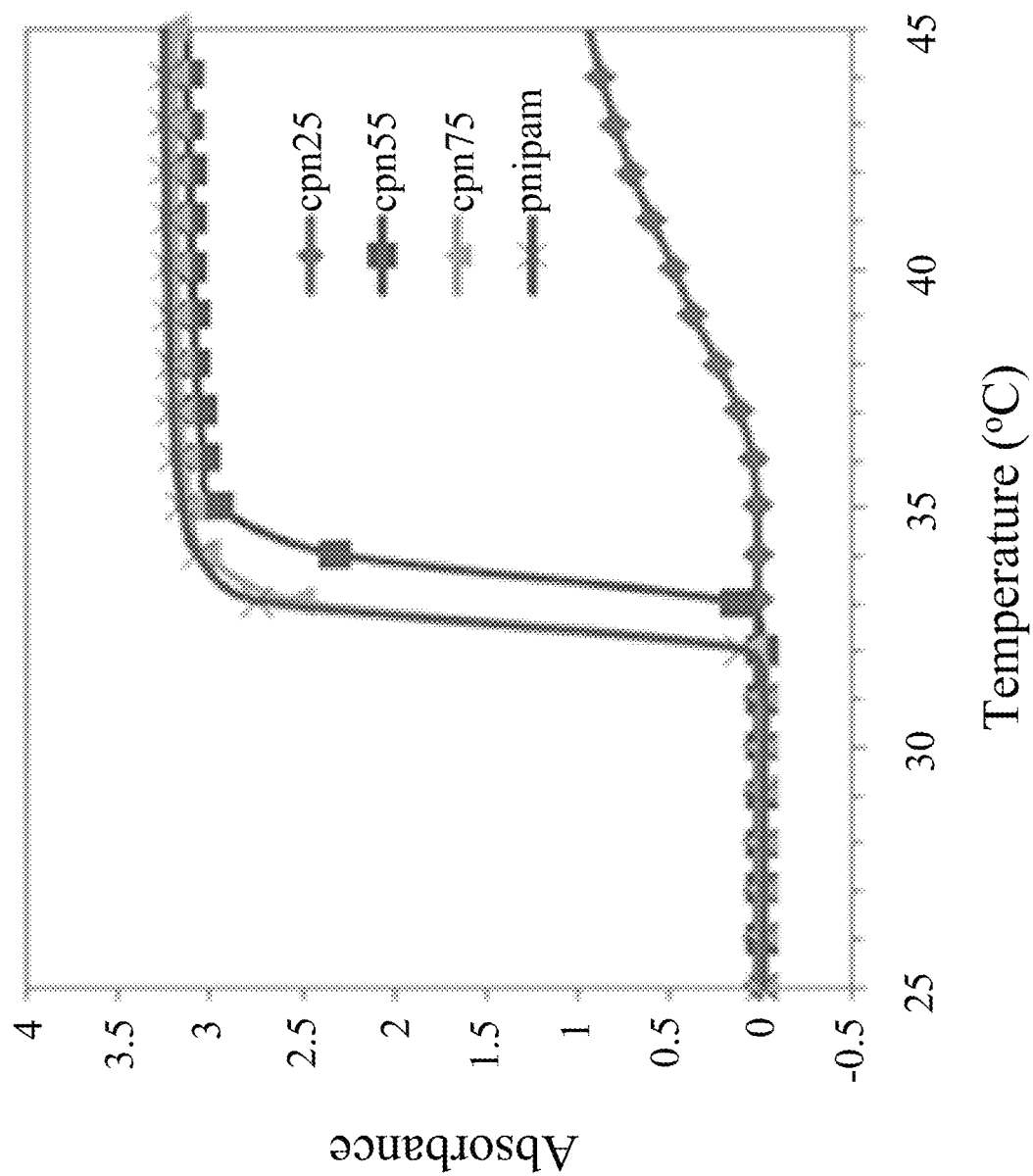
FIG. 5 shows phase transition curves of PNIPAM homopolymer and CPN copolymers with different ratios CPEGD and PNIPAM in aqueous solution as measured using compositions in aqueous solution as measured using a Jasco-815 CD spectrophotometer at 550 nm.

As used herein, the term CPN55 refers to a poly(citric acid-co-PEG-N-isopropylacrylamide) copolymer prepared with a CPEGD/NIPAM feed ratio (w/w) of 50:50. The term CPN75 refers to a poly(citric acid-co-PEG-N-isopropylacrylamide) copolymer prepared with a CPEGD/NIPAM feed ratio (w/w) of 25:75. The obtained copolymers showed the phase transition behavior between room temperature and body temperature. FIGS. 4 and 5 illustrate the temperature-dependent turbidity-concentration relationship. The CPEGD prepolymer did not show a phase transition, compared with the mixture of CPEGD prepolymer and PNIPAM homopolymer. CPN55 and CPN75 polyelectrolytes exhibited sharp thermo-precipitation at about 33° C. and 32° C. respectively, which are their lower critical solution temperatures (LCST). With the increasing content of PEG, the LCSTs of CPN polyelectrolytes decreased. In particular, the CPN55 polyelectrolyte at a concentration of 40 mg/ml reversibly and quickly formed a solid at 37° C.

Figure 6:
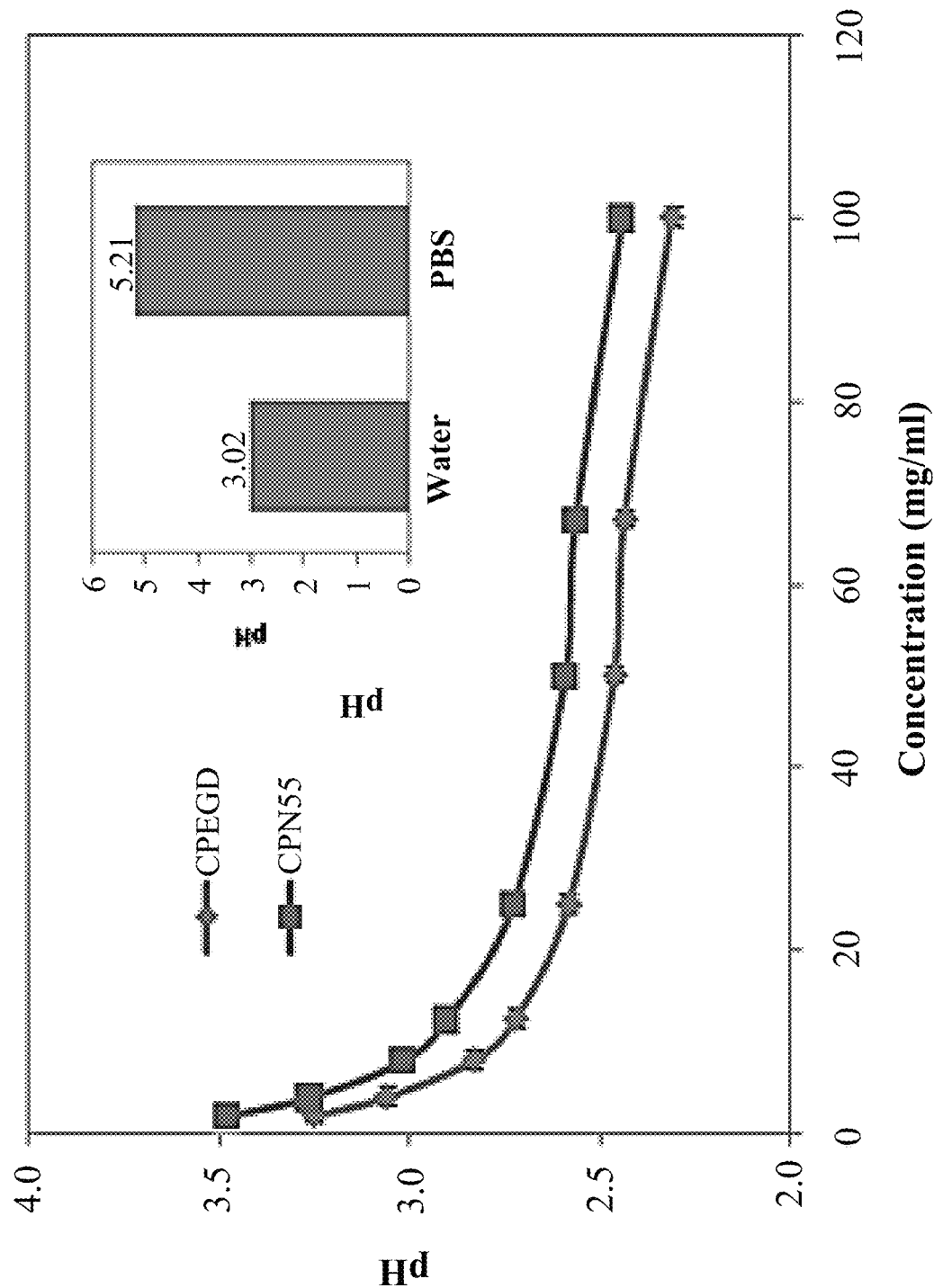
FIG. 6 shows the pH of the CPEGD prepolymer and CPN55 polyelectrolyte in aqueous solution with increasing concentrations.

CPEGD prepolymers synthesized by step growth polymerization exhibited unreacted carboxylic groups due to the tri-functional species of citric acid such that the CPN copolymer was essentially a polyelectrolyte of negative charge. The pH of CPN55 polyelectrolyte at 10 mg/ml was 3.02+0.3 in aqueous solution and 5.21±0.5 in PBS buffer. With the increasing concentrations of CPN55 polyelectrolyte in PBS solution, the polyelectrolyte exhibited more acidity as shown in FIG. 6.

Example 4

Biodegradation of Thermoresponsive CPN Polyelectrolytes

Thermoresponsive CPN polyelectrolytes with different concentrations were produced in PBS buffer at room temperature, and solidified at 37° C. These samples with 2 ml PBS (pH=7.4) buffer on the top were incubated at 37° C., then the media were removed and mass losses of these thermoresponsive CPN polyelectrolytes were measured in predefined time points after lyophilization to evaluate the degradation.

Thermoresponsive CPN polyelectrolytes with different concentrations degraded over time in PBS solution, and the mass loss increased with the increasing $H_2O$ content contained in the hydrogels in agreement with their corresponding concentrations.

Example 5

Release of Protamine and Nitric Oxide from Thermoresponsive Complexes

Figure 7:
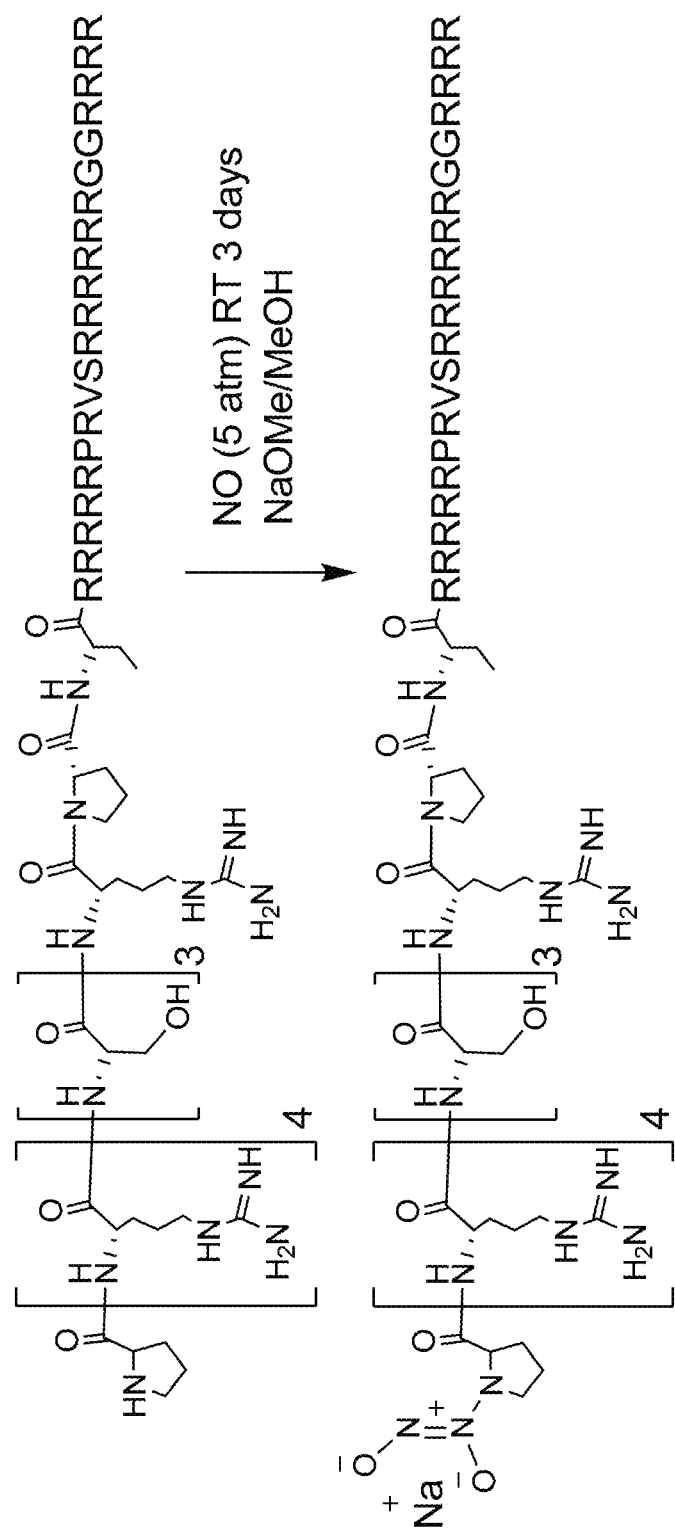
FIG. 7 is a schematic of the diazeniumdiolation of protamine sulfate at room temperature under 5 atm. NO gas.

Diazeniumdiolation of Protamine Sulfate:

The synthetic scheme for the diazeniumdiolation of protamine sulfate is shown in FIG. 7. Protamine sulfate (PS) salt from salmon (Sigma, Milwaukee, Wis.) was used as an NO carrier due to the numerous guanidinium and secondary amide moieties in the macromolecular chain which can be functionalized to diazeniumdiolate groups. N-diazeniumdiolated protamine sulfate (PSNO) was obtained by NO treatment of PS. 500 mg PS was dispersed into 10 mL of sodium methoxide (NaOMe), placed in a pressure bottle and treated with 5 atm pressurized NO gas for three days. The resulting residue was vacuum-dried and stored in a vacuum desiccator, light-protected at room temperature.

Figure 8:
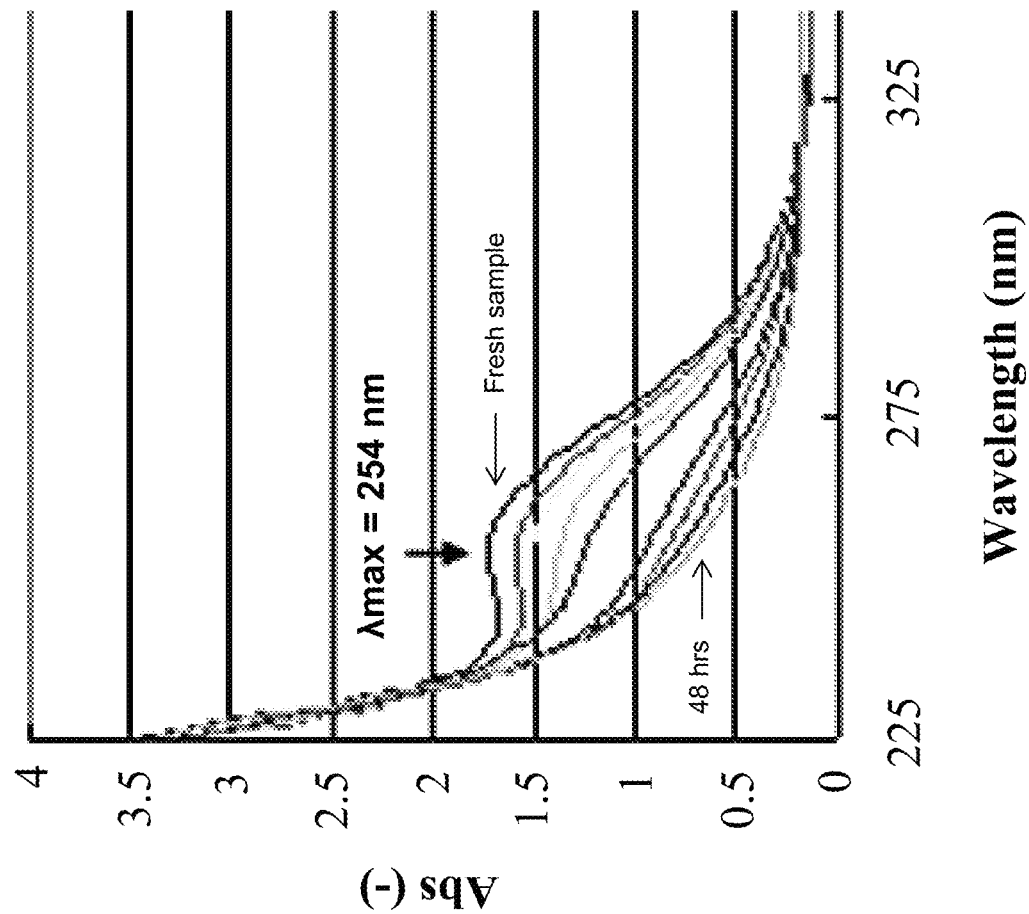
FIG. 8 shows the UV-VIS spectrum of N-Diazeniumdiolated protamine sulfate at 37° C. in PBS over time. The spectrum was taken with a fresh sample and then again after 15 minutes, 30 minutes, 1 hour, 2 hours, 4 hours, 8 hours, 24 hours, and 48 hours incubation in PBS at 37° C. The peak at 254 nm disappeared gradually over time following first-order kinetics.
Figure 9:
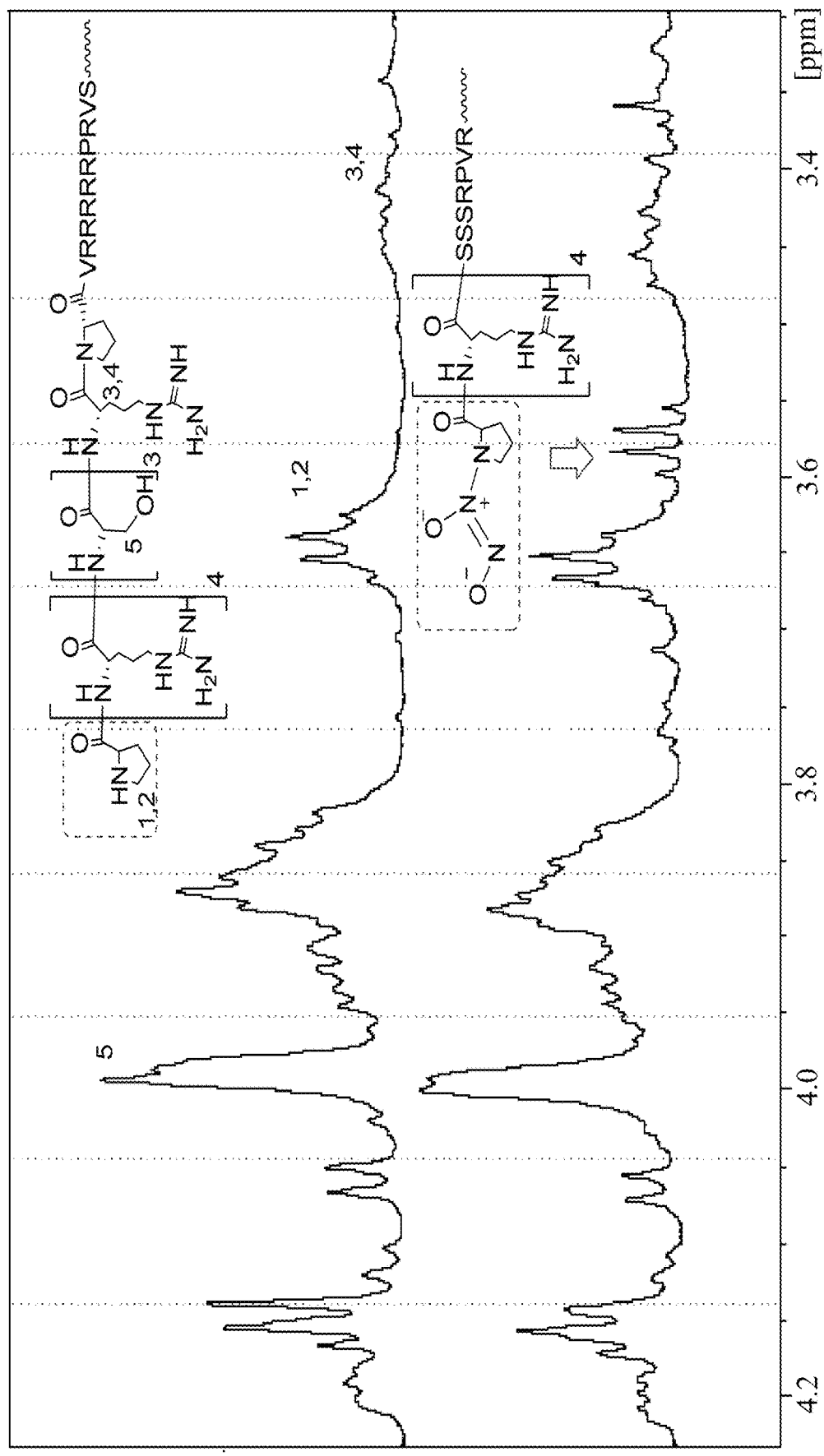
FIG. 9 shows the Proton NMR spectra of protamine sulfate (PS) before and after NO loading.

After PS was treated with 5 atm pressurized NO-gas for 3 days in NaOMe with and without a solvent, a successful conversion of PS to an NO donor (PSNO) was achieved as indicated by the peak at 254 nm (FIG. 8). The peak gradually disappeared during the first 2 days following first-order kinetics. Total nitrite content, equivalent to the NO released, was measured in samples after 2 days. The total nitrite release that could be obtained from diazeniumdiolated PS was 201.8±3.7 µmol/g PS when NaOMe was used as the solvent, an approximately 500-fold increase in NO-loading when compared to solvent-free conversion of PS which was 0.4±0.07 µmol/g PS. FIG. 9 shows the Proton NMR spectra of protamine sulfate (PS) before and after NO loading.

Release of NO and Protamine Sulfate from Thermoresponsive CPN Complexes:

Thermoresponsive CPN polyelectrolytes were dissolved into PBS buffers to form the solutions of different concentrations such as 40 mg/ml, 70 mg/ml, 100 mg/ml, 130 mg/ml, 160 mg/ml. PS and PSNO were added into the polyelectrolyte solutions to obtain 10 mg/ml PS solutions. NO release in vitro was measured in a PBS solution at 37° C. At specific time points solutions were centrifuged, decanted and refilled with fresh PBS. The decanted solution was used to assess nitrite amounts by Griess assay. Briefly, 100 µl samples were pipetted into a 96-well microtiter plate, neutralized with 0.5M HCl, and chilled to 4° C. Then 40 µl of a 1:1 mixture of 6M HCl and 12.5 mM sulfanilamide were added for 10 min at 4° C. 20 µl of 12.5 mM N-(naphthyl)-ethylenediamine dihydrochloride (NEDA) was then added to form an azo compound whose concentration is directly proportional to the concentration of nitrite. After 15 min of incubation at room temperature, the concentration of the azo compound can be determined by its maximum absorbance at 540 nm as measured via a Labsystems Muhiskan RC 96-well microtiter plate reader. The measurement of nitrites as a direct stoichiometric derivative of NO is commonly used for NO release measurements. PS amounts were determined using a standard micro-BCA assay, 100 µl samples were pipetted into a 96-well microtiter plate, then 100 µl of the Micro-BCA reagent mixture was added to each well and mixed thoroughly on a plate shaker for 30 seconds. The plate was covered using Sealing Tape for 6-Well Plates and incubated at 37° C. for about 2 hours. The plate was then cooled to room temperature and the absorbance measured at or near 562 nm on a plate reader.

Figure 10:
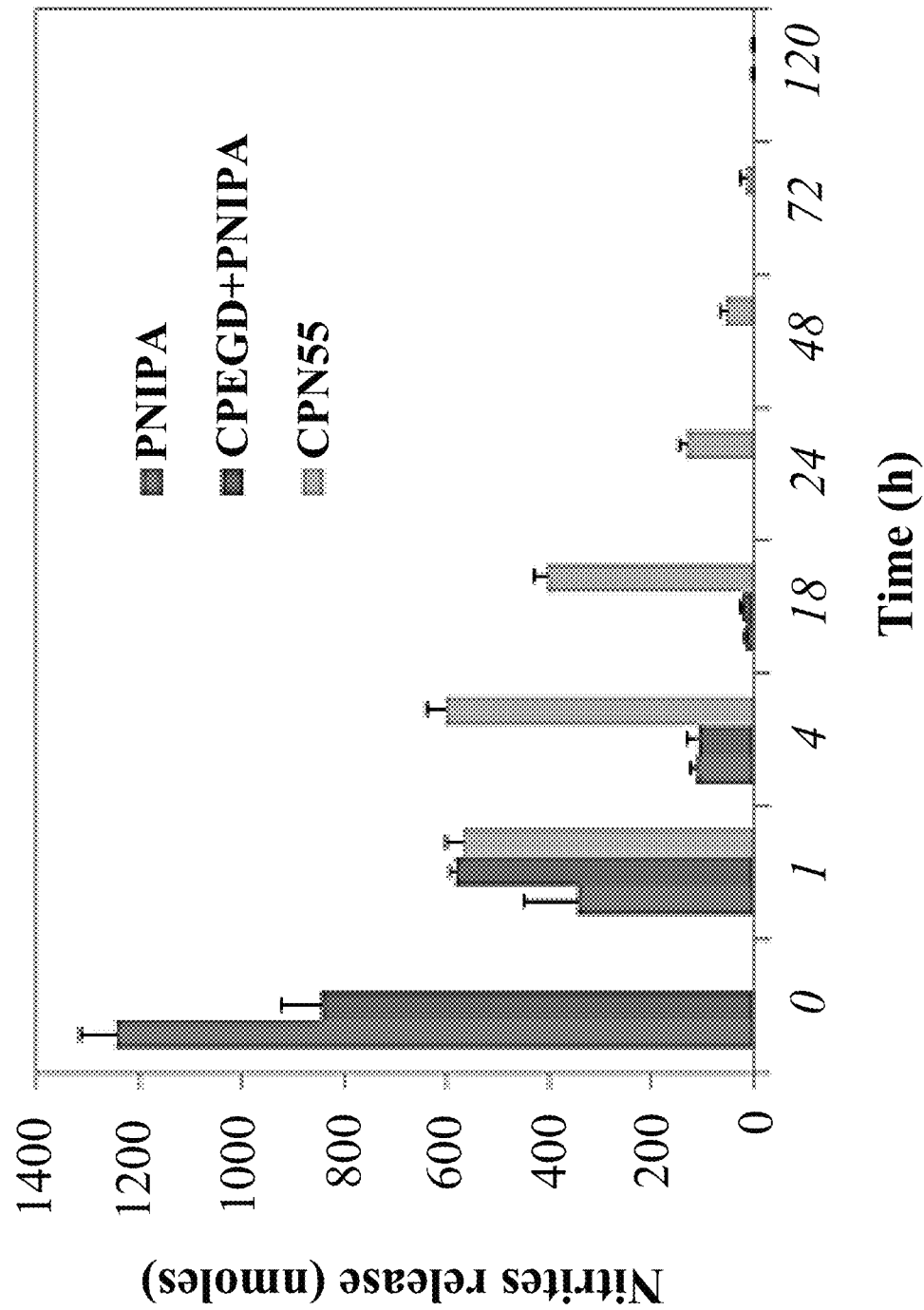
FIG. 10 shows the release of NO from PNIPAM homopolymer, the mixture of CPEGD and PNIPAM, and CPN 55 with PSNO at different times (mean+/−SD; n=3).
Figure 11:
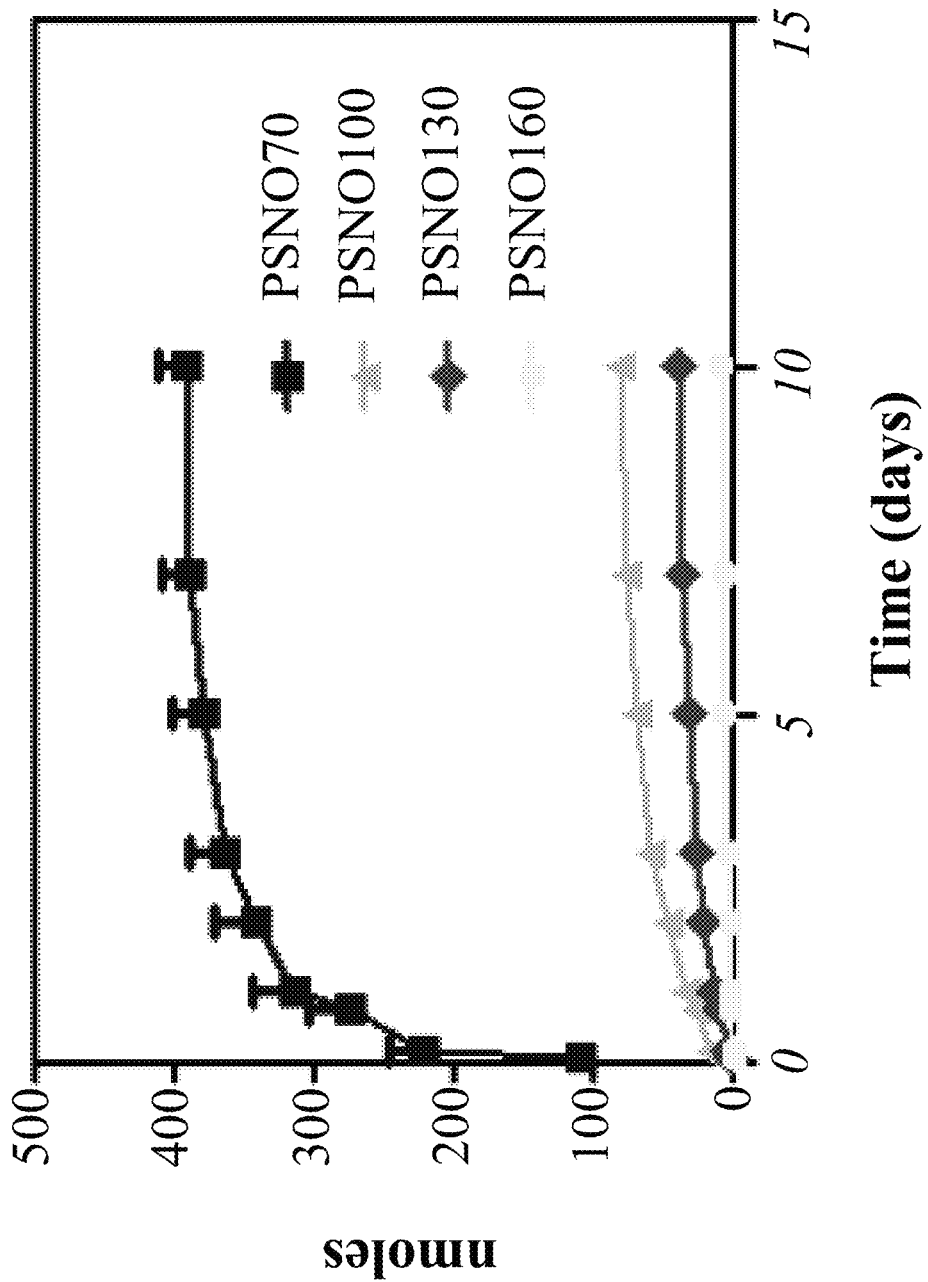
FIG. 11 shows NO release over time from CPN55:PSNO complexes prepared at concentrations of 70 mg/ml, 100 mg/ml, 130 mg/ml, and 160 mg/ml CPN55 (mean+/−SD; n=3).

Results showed that all NO was released from the PNIPAM homopolymer and the mixture of CPEGD and PNIPAM in less than 1 day (FIG. 10); however, the NO release from CPN55 complexes was strongly affected by the concentration of the CPN55 complex. NO is released from CPN55 complexes of 40 mg/ml over up to 5 days and from CPN55 complexes of 100 mg/ml over up to 2 weeks. As shown in FIG. 11, CPN55 complexes of 160 mg/ml showed the lowest release rate of NO. The release profiles indicated that NO release can be controlled by the concentration of CPN complexes in the solution.

Example 6

Cytocompatibility of Thermoresponsive CPN Polyelectrolytes

Human aortic smooth muscle cells (HASMC) were cultured in a 250 ml culture flask with SmGM-2 medium (Clonetics, Walkersville, Md.) supplemented with insulin, human fibroblast growth factor-β(hFGF-β), Gentamicin sulfate amphotericin B, fetal bovine serum (FBS) and human recombinant epidermal growth factor (hEGF). Upon 80-90% confluency, the cells were passaged or used for experiments. All the thermoresponsive polymer samples with different concentrations in PBS buffer were sterilized under UV light exposure overnight. For all the experiments, the cells were seeded into 48 well plates (Falcon) at a density of 12,000 cells per well. Following seeding, the cells were incubated with PNIPA of 20 mg/ml and 40 mg/ml and CPN polyelectrolyte of 50 mg/ml and 100 mg/ml at 37° C. and 5% CO2 in a humid environment for 1, 3, 5, or 7 days. The morphology of attached cells was observed and recorded at 24 h after cell seeding with an inverted light microscope (Nikon Eclipse, TE2000-U) equipped with a Photometrics CoolSNAP HQ (Silver Spring, Md.).

The solutions quickly gelled in several minutes, indicated that the cells were entrapped into CPN55 hydrogels which can effectively immobilize cells and serve as extracellular matrix. The cells survived and spread in the CPN55 gels after 7 days. The cell morphologies in CPN polyelectrolytes of 50 mg/ml and 100 mg/ml indicated that cells can survive in the hydrogels and that the cells are retained longer when the gels are prepared at higher concentrations of polyelectrolyte.

We claim:

1. A composition comprising, in an aqueous solvent, a copolymer of:
   (a) an N-alkyl acrylamide residue; and
   (b) a polyester comprising: citric acid, polyethylene glycol, and glycerol 1,3-diglycerolate diacrylate.

2. The composition of claim 1, wherein the alkyl is selected from: methyl, ethyl, propyl, isopropyl and cyclopropyl.

3. The composition of claim 2, in which said N-alkyl acrylamide residue comprises N-isopropylacrylamide.

4. The composition of claim 1, wherein said polyester consists of: citric acid, polyethylene glycol, and glycerol 1,3-diglycerolate diacrylate.

5. The composition of claim 1, wherein the copolymer has a lower critical solution temperature below 37° C.

6. The composition of claim 1, wherein the copolymer has a lower critical solution temperature of between 30° C. and 35° C.

7. The composition of claim 1, further comprising a positively charged compound complexed to the copolymer.

8. The composition of claim 7, wherein the positively charged compound is protamine sulfate.

9. The composition of claim 8, wherein the protamine sulfate is diazeniumdiolated.

10. The composition of claim 1, further comprising one or more active agents selected from: an antiseptic, an antibiotic, an analgesic, an anesthetic, a chemotherapeutic agent, a clotting agent, an anti-inflammatory agent, a metabolite, a cytokine, a chemoattractant, a hormone, a steroid, a protein, and a nucleic acid.

11. The composition of claim 1, further comprising one or more biological materials selected from a cell, a protein or a virus.

12. A method of growing cells, comprising introducing cells into a composition of claim 1 to produce a cell construct and incubating the culturing mixture under conditions suitable for growth of the cells.

13. The method of claim 12, wherein the composition is administered to a patient and patient's cells migrate into the composition.

* * * * *